United States Patent
Chen et al.

(10) Patent No.: US 7,067,455 B2
(45) Date of Patent: Jun. 27, 2006

(54) COPPER MODIFIED CATALYSTS FOR OXIDATIVE DEHYDROGENATION

(75) Inventors: Zhen Chen, Ponca City, OK (US); Steven R. McDonald, Ponca City, OK (US); Shang Y. Chen, Oklahoma City, OK (US); Stephan Basso, Eguisheim (FR); Charles R. Rapier, Ponca City, OK (US); Angela R. Bailey-Rivers, Ponca City, OK (US); Cemal Ercan, Tulsa, OK (US)

(73) Assignee: ConocoPhillips Company, Houston, TX (US)

(*) Notice: Subject to any disclaimer, the term of this patent is extended or adjusted under 35 U.S.C. 154(b) by 66 days.

(21) Appl. No.: 10/719,319

(22) Filed: Nov. 21, 2003

(65) Prior Publication Data
US 2005/0113247 A1    May 26, 2005

(51) Int. Cl.
*B01J 23/00* (2006.01)
*B01J 23/32* (2006.01)
*B01J 23/56* (2006.01)
*B01J 23/02* (2006.01)
*B01J 23/16* (2006.01)

(52) U.S. Cl. .............. 502/325; 502/305; 502/324; 502/331; 502/332; 502/340; 502/345; 502/349; 502/353

(58) Field of Classification Search ......... 502/305–355
See application file for complete search history.

(56) References Cited

U.S. PATENT DOCUMENTS

| | | | |
|---|---|---|---|
| 354,179 A | 12/1886 | Burnham | |
| 3,678,124 A | 7/1972 | Stepanov et al. | 260/680 E |
| 3,988,259 A * | 10/1976 | Ray | 502/25 |
| 4,162,234 A | 7/1979 | Grasselli et al. | 252/432 |
| 4,250,346 A | 2/1981 | Young et al. | 585/658 |
| 4,484,013 A * | 11/1984 | Schmidt | 568/899 |
| 4,711,870 A | 12/1987 | Yamada et al. | 502/303 |
| 4,751,336 A | 6/1988 | Jezl et al. | 585/324 |
| 4,886,931 A | 12/1989 | Bartek et al. | 585/500 |
| 4,940,826 A | 7/1990 | Font Freide et al. | 585/600 |
| 5,028,577 A * | 7/1991 | Michaels et al. | 502/243 |
| 5,211,684 A | 5/1993 | Shannon et al. | 131/352 |
| 5,382,741 A | 1/1995 | Astbury et al. | 585/652 |

(Continued)

FOREIGN PATENT DOCUMENTS

EP        0 164 864        12/1985

(Continued)

OTHER PUBLICATIONS

Yokoyama et al., "*Platinum-Tin and Platinum-Copper Catalysts for Autothermal Oxidative Dehydrogenation of Ethane to Ethylene*", Catalysis Letters, 38, (1996), pp. 181-188. No month.

*Primary Examiner*—J. A. Lorengo
*Assistant Examiner*—Patricia L. Hailey
(74) *Attorney, Agent, or Firm*—Conley Rose P.C.

(57) ABSTRACT

Catalysts and methods useful for the production of olefins from alkanes via oxidative dehydrogenation (ODH) comprise at least one base metal and copper with an optional promoter. The catalyst preferably comprises a base metal and a copper-modified Groups 8, 9, or 10 metal on a support comprising alumina, zirconia, or mixtures thereof. Copper is preferably present in an amount of from about 0.1 to about 1.0 percent by weight of the total catalyst weight. The base metal preferably comprises manganese, chromium, gold, their corresponding oxides, or combinations thereof. The optional promoter preferably comprises platinum, palladium, iridium, rhodium, ruthenium, or any combinations thereof.

30 Claims, 1 Drawing Sheet

U.S. PATENT DOCUMENTS

| | | | |
|---|---|---|---|
| 5,550,309 A * | 8/1996 | Maunders et al. | 585/654 |
| 5,905,180 A | 5/1999 | Yokoyama et al. | 585/658 |
| 6,072,097 A | 6/2000 | Yokoyama et al. | 585/658 |
| 6,365,543 B1 * | 4/2002 | Schmidt et al. | 502/325 |
| 6,417,376 B1 * | 7/2002 | Yeh et al. | 549/248 |
| 6,500,781 B1 * | 12/2002 | Luo et al. | 502/326 |
| 6,548,447 B1 * | 4/2003 | Yokoyama et al. | 502/331 |
| 6,624,116 B1 | 9/2003 | Bharadwaj et al. | 502/514 |
| 6,846,773 B1 * | 1/2005 | Yokoyama et al. | 502/339 |
| 2002/0087042 A1 | 7/2002 | Schmidt et al. | 585/654 |
| 2003/0191020 A1 * | 10/2003 | Bharadwaj et al. | 502/334 |
| 2003/0208095 A1 * | 11/2003 | Budin et al. | 585/658 |
| 2004/0068148 A1 * | 4/2004 | Allison et al. | 585/16 |
| 2004/0225165 A1 * | 11/2004 | Allison et al. | 568/910.5 |

FOREIGN PATENT DOCUMENTS

| | | |
|---|---|---|
| EP | 0 178 853 | 4/1986 |
| EP | 0 332 289 | 9/1998 |
| WO | WO 00/43336 | 7/2000 |
| WO | WO 01/47842 | 7/2001 |
| WO | WO 01/47843 | 7/2001 |
| WO | WO 01/68571 | 9/2001 |

* cited by examiner

COPPER MODIFIED CATALYSTS FOR OXIDATIVE DEHYDROGENATION

CROSS-REFERENCE TO RELATED APPLICATIONS

Not Applicable.

STATEMENT REGARDING FEDERALLY SPONSORED RESEARCH OR DEVELOPMENT

Not Applicable.

TECHNICAL FIELD OF THE INVENTION

This invention relates to catalysts and processes for oxidative dehydrogenation (ODH) of hydrocarbons. More particularly, this invention relates to copper-based ODH catalysts and to ODH processes that use these ODH catalysts to produce alkenes from alkanes. The ODH catalysts comprise a base metal, copper and optionally a promoter. According to a preferred embodiment, copper is included with a promoter and applied as a copper-modified promoter to a catalyst that includes a base metal and a support.

BACKGROUND OF THE INVENTION

Natural gas comprises several components, including alkanes. Alkanes are saturated hydrocarbons—i.e., compounds consisting of hydrogen (H) and carbon (C)—whose molecules contain carbon atoms linked together by single bonds. The principal alkane in natural gas is methane; however, significant quantities of longer-chain alkanes such as ethane ($CH_3CH_3$), propane ($CH_3CH_2CH_3$) and butane ($CH_3CH_2CH_2CH_3$) are also present. Unlike even longer-chain alkanes, these so-called lower alkanes are gaseous under ambient conditions.

There is a particular interest in the chemical conversion of the lower alkanes in natural gas, for a variety of reasons. First, vast reserves of natural gas have been found in remote areas where no local market exists. There is great incentive to exploit these natural gas formations because natural gas is predicted to outlast liquid oil reserves by a significant margin. Unfortunately, though, the economic value of natural gas in remote areas is limited, and the transportation costs for natural gas from these remote sites are generally prohibitive, primarily because of the extremely low temperatures needed to liquefy this volatile gas for transport. Consequently, there is considerable interest in techniques for converting components of natural gas to higher value and/or more easily transportable products at these remote sites. One such class of reactions involves the chemical conversion of natural gas, a relatively low value material, to higher value products such as gasoline, diesel, jet fuels, alcohols, olefins, or lubricating oils.

Several hydrocarbon processing techniques are currently being investigated for the chemical conversion of lower alkanes. One such technique involves the conversion of methane to higher chain-length alkanes that are liquid or solid at room temperature. This conversion of methane to higher hydrocarbons is typically carried out in two steps. In the first step, methane is converted with an oxidant to produce a mixture of carbon monoxide and hydrogen known as synthesis gas or syngas. In a second step, the syngas is converted to liquid hydrocarbon fuels and solid hydrocarbon waxes using the Fischer-Tropsch synthesis. The high molecular weight waxes thus produced provide an ideal feedstock for hydrocracking, which ultimately yields jet fuel, gasoline, high-decane diesel fuel, or blending stocks for such fuels.

A second factor driving research into commercial methods for chemical conversion of lower alkanes is their abundant supply at many refineries, and the relatively few commercially-viable means of converting them to more valuable products.

Alkenes are higher value chemicals than their corresponding alkanes. This is true, in part, because alkenes are important feedstocks for producing various commercially useful materials such as detergents, high-octane gasolines, pharmaceutical products, plastics, synthetic rubbers and viscosity additives. In the commercial production of plastics, elastomers, man-made fibers, adhesives, and surface coatings, a tremendous variety of polymers are used. By far the most important industrial polymers are polymerized olefins, which comprise virtually all commodity plastics. Ethylene, a raw material in the production of polyethylene, is the one of the most abundantly produced chemicals in the United States and cost-effective methods for producing ethylene are of great commercial interest.

Olefins, also called alkenes, are unsaturated hydrocarbons (compounds containing hydrogen [H] and carbon [C]) whose molecules contain one or more pairs of carbon atoms linked together by a double bond. The olefins are classified in either or both of the following ways: (1) as cyclic or acyclic (aliphatic) olefins, in which the double bond is located between carbon atoms forming part of a cyclic (closed-ring) or an open-chain grouping, respectively, and (2) as monoolefins, diolefins, triolefins, etc., in which the number of double bonds per molecule is, respectively, one two, three, or some other number. Hence, olefins are highly desired for the production of plastics.

Generally, olefin molecules are commonly represented by the chemical formula $CH_2\!=\!CHR$, where C is a carbon atom, H is a hydrogen atom, and R is an atom or pendant molecular group of varying composition. The composition and structure of R determines which of the huge array of possible properties will be demonstrated by the polymer. More specifically, acyclic monoolefins have the general formula $C_nH_{2n}$, where n is an integer. Acyclic monoolefins are rare in nature but are formed in large quantities during the cracking of petroleum oils to gasoline. The lower monoolefins, i.e., ethylene, propylene, and butylene, have become the basis for the extensive petrochemicals industry. Most uses of these compounds involve reactions of the double bonds with other chemical agents. Acyclic diolefins, also known as acyclic dialkenes, or acyclic dienes, with the general formula $C_nH_{2n-2}$, contain two double bonds; they undergo reactions similar to the monoolefins. The best-known dienes are butadiene and isoprene, used in the manufacture of synthetic rubber.

Olefins containing two to four carbon atoms per molecule are gaseous at ordinary temperatures and pressure; those containing five or more carbon atoms are usually liquid at ordinary temperatures. Additionally, olefins are only slightly soluble in water.

Olefins have traditionally been produced from alkanes by fluid catalytic cracking (FCC) or steam cracking, depending on the size of the alkanes. Heavy olefins are herein defined as containing at least five carbon atoms and are produced by FCC. Light olefins are defined herein as containing two to four carbon atoms and are predominantly produced by steam cracking.

The FCC process is a catalytic thermal process, while steam cracking is a direct, non-catalytic dehydrogenation process. FCC and steam cracking are known to have drawbacks. For example, both processes are endothermic, meaning that heat energy must be supplied to drive the reaction. In addition, in FCC, coke forms on the surface of the catalyst during the cracking processes, covering active sites and deactivating the catalyst. During regeneration, the coke is burned off the catalyst to restore its activity and to provide heat needed to drive the cracking. This cycle is very stressful for the catalyst; temperatures fluctuate between extremes as coke is repeatedly deposited and burned off. Furthermore, the catalyst particles move at high speed through steel reactors and pipes, where wall contacts and interparticle contacts are impossible to avoid. The conversion of alkanes to alkenes in both FCC and steam cracking processes may be via multi reaction steps but overall reaction can be explained as a dehydrogenation reaction. One example of such a dehydrogenation reaction is the conversion of ethane to ethylene (Reaction 1):

$$C_2H_6 + Heat \rightarrow C_2H_4 + H_2 \tag{1}$$

FCC and steam cracking units are large and expensive because catalyst regenerator and its catalysts use typically precious metals, and because the steam cracking unit requires furnaces to generate heat energy for the conversion of alkane to alkene. Recently, there has been increased interest in oxidative dehydrogenation (ODH) as an alternative to FCC and steam cracking for the production of olefins. In ODH, alkanes are dehydrogenated in the presence of an oxidant such as molecular oxygen, typically in a short contact time reactor containing an ODH catalyst. The net ODH reaction, for example as depicted in [Reaction 2] for the conversion of ethane and oxygen to ethylene and water.

$$C_2H_6 + \tfrac{1}{2}O_2 \rightarrow C_2H_4 + H_2O + Heat \tag{2}$$

Reaction 2 may be viewed as the combination of two separate reactions: a strong exothermic combustion of alkanes [Reaction 3] and an endothermic dehydrogenation of alkanes [Reaction 4].

$$C_2H_6 + O_2 \rightarrow CO_2 + H_2O + Heat \tag{3}$$

$$C_2H_6 + Heat \rightarrow C_2H_4 + H_2 \tag{4}$$

Because the exothermic combustion provides most of the heat necessary to drive the endothermic dehydrogenation reaction, ODH is a substantially autothermal process and requires no or very little energy to initiate the reaction. Energy savings over traditional, endothermal processes (FCC and steam cracking) can be significant if the heat produced with ODH is recaptured and recycled. In addition, the capital costs for olefin production via ODH are significantly less than with the traditional processes, because ODH uses simple fixed bed reactor designs and high volume throughput.

Although ODH involves the use of a catalyst, which is referred to herein as an ODH catalyst, and is therefore literally a catalytic dehydrogenation, ODH is distinct from what is normally called "catalytic dehydrogenation" in that the former involves the use of an oxidant and the latter does not.

Oxidative dehydrogenation of hydrocarbons (ODH) with short contact time reactors is an alternative to traditional steam cracking and non-oxidative dehydrogenation processes. During an ODH reaction, an oxidant, preferably molecular oxygen, is co-fed with saturated hydrocarbons, optionally balanced with an inert gas, at a gas hourly space velocity (GHSV) of about 20,000 to 10,000,000 hr$^{-1}$. The oxidant may be fed as pure molecular oxygen, air, oxygen-enriched air, oxygen mixed with a diluent, and so forth. Oxidant in the desired amount may be added in the feed to the dehydrogenation zone. The contact time of the reactants with the catalyst is typically in the 1 to 200 ms range. The reaction pressure range is typically between 0.8 bar and 5 bars (about 80 kPa–500 kPa), and the reaction temperature is typically between 800–1100° C.

Successful commercialization of an ODH process depends on the efficacy of the catalyst. In other words, successful commercial scale operation for catalytic hydrocarbon processing depends upon high hydrocarbon feedstock conversion at high throughput and with acceptable selectivity for the desired reaction products. In turn, the yield and selectivity of an ODH catalyst system are affected by several factors. One of the most important of these factors is the catalyst composition, which significantly affects not only the yields and product distributions but also the overall economics of the process. Unfortunately, few catalysts offer both the performance and cost necessary for economical large-scale industrial use.

Catalyst cost is one of the most significant economic considerations in ODH processes. Non-oxidative dehydrogenation reactions frequently employ relatively inexpensive iron-oxide based catalysts. In contrast, ODH catalysts typically utilize relatively expensive precious metals, e.g., platinum, as promoters that assist in the combustion reaction. In order to reduce catalyst costs, therefore, it is desirable to maximize the effectiveness of the catalyst composition.

Hence, there remains a need for effective catalyst systems for olefin synthesis, so as to maximize the value of the olefins produced and thus maximize the process economics. In addition, to ensure successful operation on a commercial scale, the ODH process must be able to achieve a high conversion of the hydrocarbon feedstock at high gas hourly space velocities, while maintaining good selectivity of the process to the desired products.

BRIEF SUMMARY OF PREFERRED EMBODIMENTS

The preferred embodiments of the present invention include ODH catalysts comprising a base metal, copper and optionally a promoter. According to a preferred embodiment, copper is applied as a modifier to a catalyst that includes a base metal and a support. Copper is preferably applied at levels between about 0.0001 and 10% by weight of the total catalyst, more preferably between about 0.001 and 2%, still more preferably between about 0.01 and 2%, most preferably between about 0.01 and 1%.

The base metal of the preferred embodiments preferably comprises one or more base metals, base metal oxides, or mixed base metal/metal oxides. As used herein, "base metal" includes metals from the group consisting of metals from Groups 2, 4–7, 11–15 of the Periodic Table of the Elements (according to the New Notation IUPAC Form as illustrated in, for example, the *CRC Handbook of Chemistry and Physics*, 82$^{nd}$ Edition, 2001–2002, said reference being the standard herein and throughout), scandium, yttrium, actinium, iron, cobalt, nickel, their oxides and combinations thereof. The base metal preferably includes a metal or metal oxide from Groups 2, 4–7, 11–13 of the Periodic Table of the Elements or any combination thereof. More preferably, the base metal is selected from the group consisting of manganese, chromium, gold, their corresponding oxides, and combinations thereof. When present, the base metal is preferably present at a base metal loading of between about 0.5 and about 20 weight percent of the ODH catalyst, more preferably between about 1 to about 12, and still more preferably between about 2 and about 10 weight percent. The molar ratio of copper to the base metal is preferably about 1:20 or higher, more preferably about 1:10 or higher, and yet still more preferably between about 1:10 and about 1:2. When a promoter is used, the molar ratio of the base metal to the optional promoter metal is preferably about 10 or higher, more preferably about 15 or higher, still more preferably 20 or higher, and yet still more preferably about 25 or higher.

The promoter comprises at least one metal from Groups 8, 9, and 10 of the Periodic Table of the Elements. The promoter preferably comprises platinum, palladium, iridium, rhodium, ruthenium or any combinations thereof. The promoter metal is preferably present at a promoter metal loading of between about 0.005 and about 0.20 weight percent of the ODH catalyst, more preferably between 0.005 and 0.1, still more preferably between 0.005 and 0.075, and yet still more preferably between 0.005 and 0.05 weight percent.

In preferred embodiments, the ODH catalyst comprises a support. Preferably, the support is selected from the group consisting of zirconia, magnesium stabilized zirconia, zirconia stabilized alumina, yttrium stabilized zirconia, calcium stabilized zirconia, alumina, titania, silica, magnesia, niobia, vanadia, nitrides, silicon nitride, carbides, silicon carbide, cordierite, cordierite-alpha alumina, zircon mullite, spodumene, alumina-silica magnesia, zircon silicate, sillimanite, magnesium silicates, zircin, petalite, carbon black, calcium oxide, barium sulfate, silica-alumina, alumina-zirconia, alumina-chromia, alumina-ceria, and combinations thereof. More preferably, the refractory support comprises alumina, zirconia, silicon nitride, magnesium oxide or combinations thereof. Suitable oxides include metastable and stable phases of the foregoing, including for example, gamma and alpha alumina and other alumina phases, any of which may be referred to as "alumina".

The preferred embodiments of the present invention also include methods for performing ODH processes that employ the ODH catalysts disclosed herein. Preferably, the ODH process is performed in a short-contact time reactor (SCTR). The process preferably includes maintaining a catalyst residence time of no more than 200 milliseconds for the reactant gas mixture. Residence time is inversely proportional to space velocity, and high space velocity indicates low residence time on the catalyst, typically less than 200 ms, preferably between about 1 ms and about 200 ms. The reactant mixtures for the preferred embodiments of the present invention comprise hydrocarbons, preferably alkanes, and an oxidant, preferably a molecular oxygen-containing gas. According to some preferred embodiments, the composition of the reactant mixture is such that the atomic oxygen-to-carbon ratio is between about 0.05:1 and about 5:1. Preferably, the ODH catalyst composition and the reactant mixture composition are such that oxidative dehydrogenation promoting conditions can be maintained with a preheat temperature of about 600° C. or less. More preferably, the ODH catalyst composition and the reactant mixture composition are such that oxidative dehydrogenation promoting conditions can be maintained with a preheat temperature of about 300° C. or less. According to some preferred embodiments, the ODH processes operate at a gas-hourly space velocity of between about 20,000 and about 10,000,000 $hr^{-1}$, preferably between about 50,000 and about 4,000,000 $hr^{-1}$, at a gas temperature of between about 500° C. and about 1200° C., and at a pressure between about 75 kPa (about 10 psia) to about 5,000 kPa (725 psia), preferably at a pressure between about 100 kPa (14.7 psia) to about 1,030 kPa (150 psia). In some embodiment, the pressure could be between about 100 kPa (about 14.5 psia) to about 500 kPa (about 72.5 psia).

The preferred embodiments of the present invention also include alkenes produced from alkanes using the ODH catalysts and according to the methods described.

BRIEF DESCRIPTION OF THE DRAWING

For a more detailed understanding of the preferred embodiments, reference is made to the accompanying FIGURE, which is a plot representing the effect of copper on the ethylene yield of an ODH reaction using palladium-promoted, iridium-promoted, rhodium-promoted, or ruthenium-promoted ODH catalysts based on a manganese-modified zirconia support.

DETAILED DESCRIPTION OF PREFERRED EMBODIMENTS

Figure 1:
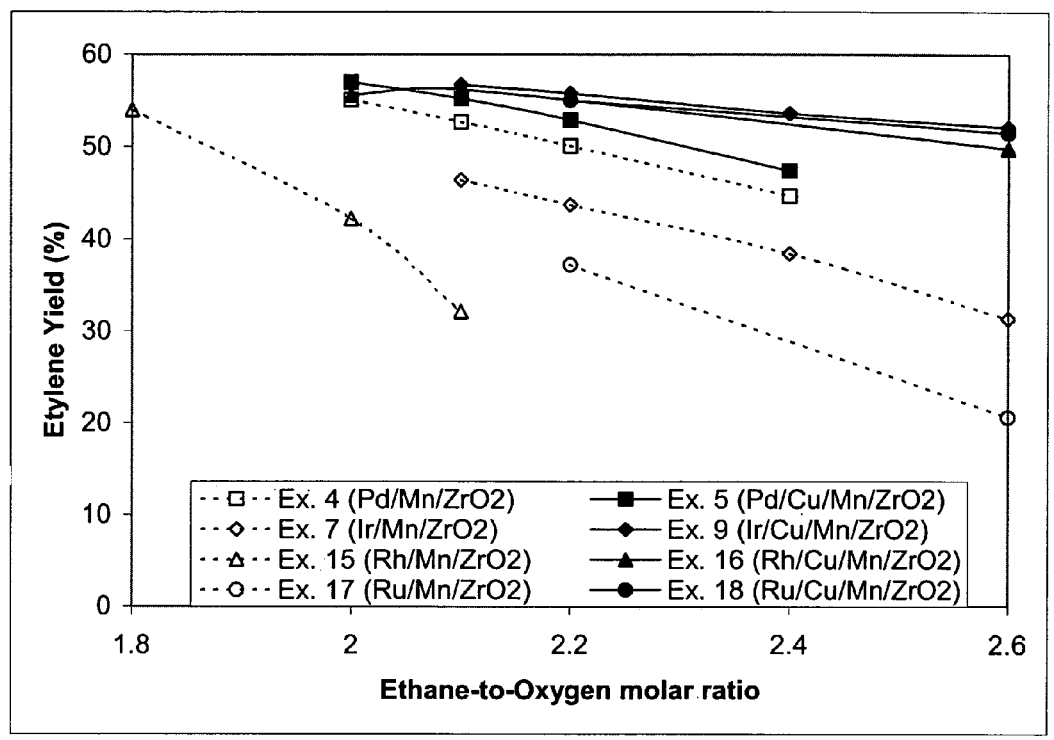

The preferred embodiments of the present invention derive from the discovery that ODH catalysts that include a base metal and copper with optionally a trace promoter metal loading can provide both high alkane conversion and alkene selectivity, even under high throughput conditions. This discovery offers the possibility of substantially improving the overall economics of ODH processing by using copper in the catalyst formulation. As used herein, the term "ODH catalyst" refers to the overall catalyst, including but not limited to, any base metal, copper, any optional promoter metal and support.

According to a preferred embodiment, copper is included and applied as a modifier to a catalyst precursor that includes a base metal and a support. The copper is preferably applied at levels between about 0.0001 and 10% by weight of the total catalyst, more preferably between about 0.001 and 2%, still more preferably between about 0.01 and 2%, most preferably between about 0.01 and 1%.

Some of the preferred embodiments of the present invention employ one or more base metals in addition to copper. A variety of base metals exhibit catalytic activity in ODH processes and are within the scope of the present invention. As an example, and without limiting the scope of the invention, base metals useful in the preferred embodiments of the present invention include Group 2 metals, Groups 4–7 metals, Group 11–15 metals, scandium, yttrium, actinium, iron, cobalt, nickel, their oxides and combinations thereof. The base metal preferably includes a metal or metal oxide from Groups 2, 4–7, and 11–13 of the Periodic Table of Elements. More preferably, the base metal is selected from the group consisting of manganese, chromium, gold, their corresponding oxides, and any combinations thereof. A combination of base metals is within the scope of the invention. Consequently, references herein to the base metal are not intended to limit the invention to one base metal.

As used herein, the term "base metal loading" refers to the percent by weight base metal in the ODH catalyst, measured as the weight of reduced base metal relative to the overall weight of the ODH catalyst. When present, the base metal is preferably present at a base metal loading of between about 0.5 and about 20 weight percent, more preferably between about 1 and about 12 weight percent, and still more preferably between about 2 and about 10 weight percent.

A variety of optional promoter metals increase catalyst activity in ODH processes and are included in the scope of the present invention. As an example, and without limiting the scope of the invention, promoter metals in ODH catalysts include metals from Groups 8, 9, and 10 of the Periodic Table. Platinum, palladium, iridium, rhodium, ruthenium, and any combinations thereof are preferred promoter metals but other promoter metals can also be used. Furthermore, a combination of promoter metals is also within the scope of the invention. Consequently, references herein to the promoter metal are not intended to limit the invention to a particular promoter metal.

As used herein, the term "promoter metal loading" refers to the percent by weight promoter metal in the ODH catalyst, measured as the weight of reduced promoter metal relative to the overall weight of the ODH catalyst. Preferably, the promoter metal loading is between about 0.005 and about 0.2 weight percent. The promoter metal loading is more preferably between about 0.005 and about 0.1, still more preferably between about 0.005 and about 0.095, and yet still more preferably between about 0.005 and about 0.05 weight percent.

The base metal and the promoter metal, if present, preferably have a molar ratio of the base metal to the optional promoter metal equal to or higher than about 10, more preferably about 15 or higher, still more preferably about 20 or higher, and yet still more preferably about 25 or higher. When the base metal is manganese and an optional promoter selected from platinum, palladium, iridium, rhodium, or ruthenium, the molar ratio of the base metal to the optional promoter metal The base metal, copper and the optional promoter are preferably deposited on a support. The support may be configured as wire gauzes, porous monoliths, or discrete particles. The term "monolith" refers to any singular piece of material of continuous manufacture such as solid pieces of metal or metal oxide or foam materials or honeycomb structures. Two or more such catalyst monoliths may be stacked in the catalyst zone of the reactor if desired. For example, the catalyst can be structured as, or supported on, a refractory oxide "honeycomb" straight channel extrudate or monolith, made of cordierite or mullite, or other configuration having longitudinal channels or passageways permitting high space velocities with a minimal pressure drop. Such configurations are known in the art and described, for example, in *Structured Catalysts and Reactors*, A. Cybulski and J. A. Moulijn (Eds.), Marcel Dekker, Inc., 1998, p. 599–615 (Ch. 21, X. Xu and J. A. Moulijn, "Transformation of a Structured Carrier into Structured Catalyst"), which is hereby incorporated herein by reference.

Some preferred monolithic supports include partially stabilized zirconia (PSZ) foam (stabilized with Mg, Ca or Y), or foams of α-alumina, cordierite, titania, mullite, Zr-stabilized α-alumina, or mixtures thereof. A preferred laboratory-scale ceramic monolith support is a porous alumina foam with approximately 6,400 channels per square inch (80 pores per linear inch). Preferred foams for use in the preparation of the catalyst include those having from 30 to 150 pores per inch (12 to 60 pores per centimeter). In a preferred embodiment, the monolith is generally cylindrical, with a diameter corresponding to the inside diameter of the reactor tube.

Alternatively, other refractory foam and non-foam monoliths may serve as satisfactory supports. The promoter metal precursor and any base metal precursor, with or without a ceramic oxide support forming component, may be extruded to prepare a three-dimensional form or structure such as a honeycomb, foam or other suitable tortuous-path structure.

More preferred catalyst geometries employ distinct or discrete particles. The terms "distinct" or "discrete" particles, as used herein, refer to supports in the form of divided materials such as granules, beads, pills, pellets, cylinders, trilobes, extrudates, spheres, other rounded shapes or another manufactured configuration. Alternatively, the divided material may be in the form of irregularly shaped particles. Preferably at least a majority—i.e., greater than about 50 percent—of the particles or distinct structures have a maximum characteristic length (i.e., longest dimension) equal to or less than ten millimeters, preferably less than three millimeters. Preferably, these particulate-supported catalysts are prepared by impregnating or washcoating the base metal, then copper with the optional promoter metal onto the particulate support.

Numerous materials, including refractory materials, may be used as supports in the present invention. Without limiting the scope of the invention, suitable support materials include zirconia, magnesium stabilized zirconia, magnesium oxide, zirconia stabilized alumina, yttrium stabilized zirconia, calcium stabilized zirconia, alumina, cordierite, titania, silica, magnesia, niobia, vanadia, nitrides, silicon nitride, carbides, silicon carbide, cordierite, cordierite-alpha alumina, zircon mullite, spodumene, alumina-silica magnesia, zircon silicate, sillimanite, magnesium silicates, petalite, carbon black, calcium oxide, barium sulfate, silica-alumina, alumina-zirconia, alumina-chromia, alumina-ceria, and combinations thereof. Preferably, the support comprises a refractory material such as alumina, zirconia, or combinations thereof. The support may be modified, stabilized, or pretreated in order to achieve the proper structural stability desired for sustaining the operationg conditions of the catalysts made therefrom. When alumina is used as support, alumina is preferably in the form of alpha-alumina (α-alumina); however, the other forms of alumina have also demonstrated satisfactory performance.

The support can be pretreated prior to application of the base metal and/or copper. The pretreatment can include heating, spray-drying to for example adjust particle sizes, dehydrating, drying, steaming and/or calcining. In the case of calcining or heating, the pretreatment step not only can stabilize the support structure, but also can bum off any impurities that may contaminate the support and that may have been introduced in the support through manufacturing and/or through handling. The support is preferably pretreated by a heat treatment at a temperature between about 1,000° C. and 1,500° C. for 0.5 to 10 hours, preferably between about 2 and about 7 hours, at a heating ramp rate between 0.5 and 3° C./min (preferably at about 1.5° C./min).

The base metal, copper, and the optional promoter metal, when present, may be deposited in or on the support by any method known in the art. Without limiting the scope of the invention, acceptable methods include incipient wetness impregnation, chemical vapor deposition, co-precipitation, and the like. Preferably, the base metal, copper and the optional promoter metal are all deposited by the incipient wetness technique.

In a particularly preferred embodiment, a first solution comprising the base metal is applied to the support using an incipient wetness technique; the resulting catalyst precursor is calcined; a second solution containing copper and optionally the promoter metal is applied; and the resulting copper-modified optionally-promoted metal catalyst is calcined again. The first solution, which contains the base metal, preferably comprises a salt of the base metal or a combination of base metal salts (anhydrous or in a hydrated form), such as for example, nitrate, acetate, acetylacetonate, ammonium nitrate, chloride, and carbonate. The second solution, which contains copper, preferably comprises a copper salt or a combination of copper salts (anhydrous or in a hydrated form), such as for example, copper nitrate, copper acetate, copper carbonate, copper chloride, copper acetylacetonate, and/or copper ammonium nitrate. When the second solution contains palladium as the promoter, it preferably contains a palladium salt or a combination of palladium salts (anhydrous or in a hydrated form) such as palladium nitrate, palladium oxide, palladium acetate, palladium chloride, palladium bromide, palladium acetylacetonate, palladium propionate, and ammonium hexachloropalladate(IV). When the second solution contains platinum as the promoter, it preferably contains a platinum salt or a combination of platinum salts (anhydrous or in a hydrated form), such ammonium hexachloroplatinate(IV), ammonium tetrachloroplatinate(II), hydrogen hexachloroplatinate(IV), acetylacetonate, hexafluoroacetyl-acetonate, potassium hexachloroplatinate(IV), platinum nitrate, platinum acetate, platinum chloride, platinum bromide, platinum acetylacetonate, platinum oxide hydrate. When the second solution contains iridium as the promoter, the second solution preferably contains an iridium salt or a combination of iridium salts, such ammonium hexachloroiridate, iridium acetylacetonate, iridium nitrate, iridium chloride, and iridium oxide. When the second solution contains rhodium as the promoter, the second solution preferably contains a rhodium salt or a combination of rhodium salts, such rhodium nitrate, rhodium carbonyl chloride (I) [$Rh_2(CO)_4Cl_2$], pentaamminechlororhodium (II) dichloride [$RhCl(NH_3)_5]Cl_2$], and rhodium (III) chloride. When the second solution contains ruthenium as the promoter, the second solution preferably contains a ruthenium salt or a combination of ruthenium salts, such as for example ruthenium carbonyl, ruthenium (III) acetylacetonate, pentaammine chloro ruthenium chloride (III) [$RuCl(NH_3)_5]Cl_2$], hexaammine ruthenium chloride [$Ru(NH_3)_6.Cl_3$], Ru(III)2,4-pentanedionoate, and ruthenium(III) nitrosyl nitrate.

The preferred embodiments of the processes of the present invention employ a hydrocarbon feedstock and an oxidant feedstock that are mixed to yield a reactant mixture, which is sometimes referred to herein as the reactant gas mixture. Preferably, the hydrocarbon feedstock comprises one or more alkanes having between two and ten carbon atoms. More preferably, the hydrocarbon feedstock comprises one or more alkanes having between two and five carbon atoms. Without limiting the scope of the invention, representative examples of acceptable alkanes are ethane, propane, butane, isobutane and pentane. The hydrocarbon feedstock preferably comprises ethane.

The oxidant feedstock comprises an oxidant capable of oxidizing at least a portion of the hydrocarbon feedstock. Appropriate oxidants may include, but are not limited to, $I_2$, $O_2$, ozone, $N_2O$, $CO_2$ and $SO_2$. Use of the oxidant shifts the equilibrium of the dehydrogenation reaction toward complete conversion through the formation of compounds containing the abstracted hydrogen (e.g., $H_2O$, HI and $H_2S$). Preferably, the oxidant comprises a molecular oxygen-containing gas. Without limiting the scope of the invention, representative examples of acceptable molecular oxygen-containing gas feedstocks include pure oxygen gas, air and $O_2$-enriched air.

As depicted in equation [4], the complete combustion of an alkane requires a stoichiometrically predictable quantity of oxygen:

$$C_nH_{2n+2} + [(3n+1)/2]O_2 \rightarrow nCO_2 + [n+1]H_2O \quad (4)$$

According to equation (4), an atomic oxygen-to-carbon ratio of 3n+1:n represents the stoichiometric ratio for complete combustion where n equals the number of carbons in the alkane. For alkanes with between 2 and 10 carbon atoms, the stoichiometric ratio of oxygen atoms to carbon atoms for complete combustion ranges between 3.5:1 and 3.1:1. Preferably, the composition of the reactant mixture is such that the atomic oxygen-to-carbon ratio is between about 0.05:1 and about 5:1.

Preferably, a short contact time reactor (SCTR) is used. Use of a SCTR for the commercial scale conversion of light alkanes to corresponding alkenes allows reduced capital investment and increases alkene production significantly. The preferred embodiments of the present invention employ a very fast contact (i.e., millisecond range)/fast quench (i.e., less than one second) reactor assembly such as those described in the literature. For example, co-owned U.S. Pat. Nos. 6,409,940 and 6,402,898 describe the use of a millisecond contact time reactor for use in the production of synthesis gas by catalytic partial oxidation of methane. The disclosures of these references are hereby incorporated herein by reference.

The ODH catalyst may be configured in the reactor in any arrangement including fixed bed, fluidized bed, or ebulliating bed (sometimes referred to as ebullating bed) arrangements. A fixed bed arrangement employs a stationary catalyst and a well-defined reaction volume whereas a fluidized bed utilizes mobile catalyst particles. Conventional fluidized beds include bubbling beds, turbulent fluidized beds, fast fluidized beds, concurrent pneumatic transport beds, and the like. A fluidized bed reactor system has the advantage of allowing continuous removal of catalyst from the reaction zone, with the withdrawn catalyst being replaced by fresh or regenerated catalyst. A disadvantage of fluidized beds is the necessity of downstream separation equipment to recover entrained catalyst particles. Preferably, the catalyst is retained in a fixed bed reaction regime in which the catalyst is retained within a well-defined reaction zone. Fixed bed reaction techniques are well known and have been described in the literature. Irrespective of catalyst arrangement, the reactant mixture is contacted with the catalyst in a reaction zone while maintaining reaction promoting conditions.

The reactant gas mixture is heated prior to or as it passes over the catalyst such that the reaction initiates. In accordance with one preferred embodiment of the present invention, a method for the production of olefins includes contacting a preheated alkane and a molecular-oxygen containing gas with a catalyst containing copper, an optional promoter, a base metal and a refractory support under conditions sufficient to initiate the oxidative dehydrogenation of the alkane, maintaining a contact time of the alkane with the catalyst for less than 200 milliseconds, and maintaining oxidative dehydrogenation promoting conditions during the contact. Preferably, the ODH catalyst composition and the reactant mixture composition are such that oxidative dehydrogenation promoting conditions can be maintained with a preheat temperature of about 600° C. or less. More preferably, the ODH catalyst composition and the reactant mixture composition are such that oxidative dehydrogenation promoting conditions can be maintained with a preheat temperature of about 300° C. or less.

Reaction productivity, conversion and selectivity are affected by a variety of processing conditions including temperature, pressure, gas hourly space velocity (GHSV) and catalyst arrangement within the reactor. As used herein, the term "maintaining reaction promoting conditions" refers to controlling these reaction parameters, as well as reactant mixture composition and catalyst composition, in a manner in which the desired ODH process is favored.

The reactant mixture may be passed over the catalyst in any of a wide range of gas hourly space velocities. Gas hourly space velocity (GHSV) is defined as the volume of reactant gas per volume of catalyst per unit time. Although for ease in comparison with prior art systems space velocities at standard conditions have been used to describe the present invention, it is well recognized in the art that residence time is inversely related to space velocity and that high space velocities correspond to low residence times on the catalyst and vice versa. High throughput systems typically employ high GHSV and low residence times on the catalyst.

Preferably, GHSV for the present process, stated as normal liters of gas per liters of catalyst per hour, ranges from about 20,000 to about 10,000,000 $hr^{-1}$, more preferably from about 50,000 to about 4,000,000 $hr^{-1}$. The GHSV is preferably controlled so as to maintain a reactor residence time of no more than about 200 milliseconds for the reactant mixture. An effluent stream of product gases including alkenes, unconverted alkanes, $H_2O$ and possibly CO, $CO_2$, $H_2$ and other byproducts exits the reactor. In a preferred embodiment, the alkane conversion is at least about 40 percent and the alkene selectivity is at least about 30 percent. More preferably, the alkane conversion is at least about 60 percent and the alkene selectivity is at least about 50 percent. Still more preferably, the alkane conversion is at least about 70 percent and the alkene selectivity is at least about 55 percent.

In some embodiments, unconverted alkanes may be separated from the effluent stream of product gases and recycled back into the feed. Product $H_2$ and CO may be recovered and used in other processes such as Fischer-Tropsch synthesis and methanol production. In some embodiments the use of steam may be employed. Steam may be used to activate the catalyst, remove coke from the catalyst via a water-gas shift reaction (WGS), or serve as a diluent for temperature control.

Hydrocarbon processing techniques frequently employ atmospheric or above atmospheric pressures to maintain reaction promoting conditions. Some embodiments of the present invention entail maintaining the reactant gas mixture at atmospheric or near-atmospheric pressures of approximately 1 atmosphere while contacting the catalyst. Advantageously, certain preferred embodiments of the process are operated at above atmospheric pressure to maintain reaction promoting conditions. Some preferred embodiments of the present invention employ pressures up to about 5,000 kPa (about 50 atmospheres), more preferably between about 100 kPa and about 4,000 kPa (between about 1 and about 40 atmospheres), most preferably between about 100 and about 1,000 kPa (between about 1 and about 10 atmospheres).

EXAMPLES

The invention having been generally described, the following examples are given as particular embodiments of the invention and to demonstrate the practice and advantages hereof. It is understood that the examples are given by way of illustration and are not intended to limit the specification or the claims to follow in any manner.

The following EXAMPLES 1–18 illustrate the effect of various catalyst compositions on the ODH process. For all catalyst EXAMPLES 1–18, the base metal, copper and/or the promoter metal were added to a zirconia or alumina support using an incipient wetness technique, as is well-known in the art. Various soluble metal salts of the base metal, copper and/or the promoter metal can be employed for incipient wetness such as nitrates, acetates, chlorides, acetylacetonates or the like.

Examples 1 to 9

Catalyst Preparation for Examples 1–9

The zirconia support material used in EXAMPLES 1–9 was purchased from Süd-Chemie (Louisville, Ky.). The refractory support was comprised of particles of about 0.84–1.19 mm size (16–20 mesh size). In some catalysts, the zirconia was used with only the addition of a base metal and/or promoter metal, while in other catalysts, a base and/or a copper-modified promoter were used. For the preparation of catalyst EXAMPLES 1–9, an incipient wetness technique, as is well-known in the art, was used. The base metal was manganese in these experiments, and when it was used, it was added first to the zirconia support. Various soluble metal salts of manganese, copper and/or the promoter metal (palladium or iridium) can be employed for incipient wetness such as nitrates, acetates, chlorides, acetylacetonates or the like. For EXAMPLES 1–9, manganese nitrate [$Mn(NO_3)_2$], copper nitrate [$Cu(NO_3)_2$], palladium nitrate [$Pd(NO_3)_2$], and ammonium hexachloroiridate (III) [$(NH_4)_2IrCl_6$] were used and they were all purchased from Aldrich (Milwaukee, Wis.).

Example 1

2.4Mn/100ZrO$_2$

The zirconia support was impregnated with a solution of $Mn(NO_3)_2$ by incipient wetness technique. The amount of manganese salt was dissolved in enough water to infuse into the support particles without wetting the surface of the support, and to yield 2.4 g Mn per 100 g of zirconia support in the final catalyst. After the magnesium metal was applied, the sample was dried at 125° C. for 1 hour followed by calcination in air at 500° C. for 3 hours.

Example 2

0.4Cu/100 ZrO2

The zirconia support was impregnated with a solution of $Cu(NO_3)_2$. The same conditions for impregnation, conditioning, drying, and calcining as described in EXAMPLE 1 were used. The final composition of the catalyst was 0.4 g Cu per 100 g of zirconia support.

Example 3

0.4Cu/2.4Mn/100ZrO2

This catalyst was first prepared as described in EXAMPLE 1. Then the manganese-modified zirconia support was impregnated with a solution of $Cu(NO_3)_2$ to yield 0.4 g Cu per 100 g of support. The same conditions for impregnation, conditioning, drying, and calcining as described earlier in EXAMPLE 1 were used. The final composition of the catalyst was 0.4 g Cu per 100 g of zirconia support, 2.4 g Mn per 100 g of zirconia support.

Example 4

0.1Pd/2.4Mn/100ZrO2

This catalyst was first prepared as described in EXAMPLE 1. Then the manganese-modified zirconia support was impregnated with a solution of $Pd(NO_3)_2$ by incipient wetness technique, to yield 0.1 g Pd per 100 g of zirconia support. The same conditions for impregnation, conditioning, drying, and calcining as described in EXAMPLE 1 were used. The final composition of the catalyst was 0.1 g Pd per 100 g of zirconia support, 2.4 g Mn per 100 g of zirconia support.

Example 5

0.1Pd-0.4Cu/2.4Mn/100 ZrO2

This catalyst was first prepared as described in EXAMPLE 1. Then the manganese-modified zirconia support was impregnated with a solution of $Pd(NO_3)_2$ and $Cu(NO_3)_2$ by incipient wetness technique, to yield 0.1 g Pd and 0.4 g Cu per 100 g of zirconia support in the final catalyst. The same conditions for impregnation, conditioning, drying, and calcining as described in EXAMPLE 1 were used. The final composition of the catalyst was 0.1 g Pd, 0.4 g Cu and 2.4 g Mn per 100 g of zirconia support.

Example 6

0.02 Ir/100 ZrO2

The same procedure as for EXAMPLE 1 was used except that a solution of $(NH_4)_2IrCl_6$ was used instead of $Mn(NO_3)_2$, The final composition of the catalyst was 0.02 g Ir per 100 g of zirconia support with the remainder being zirconia.

Example 7

0.02Ir/2.6Mm100 ZrO2

This catalyst was first prepared as described in EXAMPLE 1, except that the amount of manganese loading was slightly higher at 2.6 wt %. Then the manganese-modified zirconia support was impregnated with a solution of a solution of $(NH_4)_2IrCl_6$ by incipient wetness technique, to yield 0.02 wt % Ir in the final catalyst weight. The same conditions for impregnation, conditioning, drying, and calcining as described in EXAMPLE 1 were used. The final composition of the catalyst was 0.02 g Ir and 2.6 g Mn per 100 g of zirconia support.

Example 8

0.02Ir/0.6Cu/100 ZrO2

The pretreated zirconia support was impregnated with a solution of $Cu(NO_3)_2$ and $(NH_4)_2IrCl_6$. The same conditions for impregnation, conditioning, drying, and calcining as described in EXAMPLE 1 were used. The final composition of the catalyst was 0.6 g Cu and 0.02 g Ir per 100 g of zirconia support with the remainder being zirconia.

Example 9

0.02Ir/0.6Cu/2.4Mn/100 ZrO2

This catalyst was first prepared as described in EXAMPLE 1. Then the manganese-modified zirconia support was impregnated with a solution of $Cu(NO_3)_2$ and $(NH_4)_2IrCl_6$. The same conditions for impregnation, conditioning, drying, and calcining as described in EXAMPLE 1 were used. The final composition of the catalyst was 0.02 g Ir, 0.6 g Cu, and 2.4 g Mn per 100 g of zirconia support.

Catalyst Performance Testing Procedure for EXAMPLES 1–9

Before testing, all catalyst EXAMPLES 1–9 were reduced in an atmosphere with an equimolar mixture of hydrogen and nitrogen at 125° C. for 0.5 hour, then at 500° C. for 3 hours.

Ethane, oxygen, and nitrogen came from gas cylinders and were controlled by respective gas flow controllers. They were mixed through a static mixer; then the mixture was fed to the reactor. The reactor was a ⁹⁄₁₆" inside diameter quartz tubing. The catalysts were packed between two blank ceramic foams, one as catalyst bed support and another as shield. An electric heater was located at the upstream of a catalyst bed and used to pre-heat the reactor feed to desired temperatures. A cooler was located at the downstream of a catalyst bed and used to rapidly cool product stream down to below 35° C. to condensate most of water vapor. A small part of the product gas stream was sent to a gas chromatograph for composition analyses.

The test was conducted with 0.4 gram of each of the catalysts EXAMPLES 1–9 described above. The reactant gas mixture comprised $O_2$ and ethane, and the ethane-to-$O_2$ molar ratio of the feed varied from 2.0 to 2.6, with a total reactant gas mixture flow rate of 3 standard liters per minute (SLPM), corresponding to a gas hourly space velocity of about 354,000 $hr^{-1}$. Nitrogen was present in the feed stream in an amount equal to 10 vol. %. The pre-heat temperature of the feed was 300° C. The reactor pressure was about 4 to 5 psig (128.9 to 135.8 kPa).

The results are reported in Table 1, where $C_2H_4$, $O_2$, $C_2H_2$, $CH_4$, CO, and $CO_2$ represent ethylene, molecular oxygen, acetylene, methane, carbon monoxide, and carbon dioxide. FIG. 1 illustrates the effect of copper on the ethylene yield of an ODH reaction using palladium-promoted catalysts or iridium-promoted ODH catalysts based on a manganese-modified zirconia support.

Examples 10–14

Catalyst EXAMPLES 10–14 were prepared and tested using different procedures than for catalyst EXAMPLES 1–9, therefore their method of preparation and testing procedure are described below. The base metal was again manganese in these catalysts, and when it was used, it was added first to the zirconia or alumina support. Manganese nitrate [$Mn(NO_3)_2$], copper nitrate [$Cu(NO_3)_2$], and palladium nitrate [$Pd(NO_3)_2$] used to prepare the catalyst samples for EXAMPLES 10–14 were all purchased from Aldrich (Milwaukee, Wis.).

For EXAMPLE 10, a zirconia support was purchased from Süd-Chemie (Louisville, Ky.) in the form of particles (ca. 0.84–1.19 mm size or 16–20 mesh size). The zirconia support was thermally pretreated at 1,000° C. for about 6 hours at a ramp rate of 1.5° C./min.

For EXAMPLES 11–14, were prepared using an alpha-alumina support from Saint-Gobain NorPro (Akron, Ohio) in the form of particles (ca. 1.2 mm in size). The alpha alumina support was thermally pretreated at 1,400° C. for 3 hours at a ramp rate of 1.5° C./min.

For EXAMPLES 11–14, were prepared using an alpha-alumina support from Saint-Gobain NorPro (Akron, Ohio) in the form of particles (ca. 1.2 mm in size). The alpha alumina support was thermally pretreated at 1,400° C. for 3 hours at a ramp rate of 1.5° C./min.

TABLE 1

Catalytic performance of EXAMPLES 1–9 on zirconia at about 4 psig

| | | Catalysts | $C_2H_6$ to $O_2$ | Ethane | | Selectivity, % | | | | | $C_2H_4$ |
|---|---|---|---|---|---|---|---|---|---|---|---|
| | # | Composition | ratio | Conv., % | $C_2H_4$ | $C_2H_2$ | $CH_4$ | $CO_2$ | CO | Other | yield, % |
| A | 1 | 2.4Mn/ZrO2 | 2.0 | 88.8 | 64.0 | 2.7 | 8.6 | 6.9 | 15.9 | 1.9 | 56.8 |
|   | 2 | 0.4Cu/ZrO2 |     | 76.5 | 68.2 | 0.7 | 6.6 | 6.6 | 15.7 | 2.2 | 52.2 |
|   | 3 | 0.4Cu/2.4Mn/ZrO2 | | 79.4 | 62.0 | 1.0 | 8.6 | 5.4 | 18.9 | 4.1 | 49.2 |
| B | 1 | 2.4Mn/ZrO2 | 2.1 | 85.3 | 66.9 | 1.9 | 7.9 | 7.2 | 14.8 | 1.3 | 57.1 |
|   | 2 | 0.4Cu/ZrO2 |     | 51.8 | 65.3 | 0.1 | 6.6 | 6.7 | 17.6 | 3.7 | 33.8 |
|   | 3 | 0.4Cu/2.4Mn/ZrO2 | | 79.3 | 63.6 | 1.3 | 8.6 | 6.7 | 15.4 | 4.4 | 50.4 |
| C | 1 | 2.4Mn/ZrO2 | 2.2 | 79.1 | 67.8 | 1.0 | 7.7 | 5.8 | 16.1 | 1.6 | 53.6 |
|   | 2 | 0.4Cu/ZrO2 |     | 39.8 | 64.9 | 0.0 | 6.2 | 8.4 | 16.9 | 3.6 | 25.8 |
|   | 3 | 0.4Cu/2.4Mn/ZrO2 | | 76.5 | 65.9 | 0.8 | 7.5 | 6.5 | 14.9 | 4.4 | 50.4 |
| D | 1 | 2.4Mn/ZrO2 | 2.4 | ** | ** | ** | ** | ** | ** | ** | ** |
|   | 2 | 0.4Cu/ZrO2 |     | ** | ** | ** | ** | ** | ** | ** | ** |
|   | 3 | 0.4Cu/2.4Mn/ZrO2 | | 71.6 | 69.0 | 0.6 | 6.7 | 7.3 | 12.4 | 4.0 | 49.4 |
| E | 4 | 0.1Pd/2.4Mn/ZrO2 | 2.0 | 81.2 | 67.8 | 1.9 | 6.9 | 6.4 | 15.4 | 1.6 | 55.1 |
|   | 5 | 0.1Pd—0.4Cu/2.4Mn/ZrO2 | | 84.8 | 67.2 | 3.7 | 8.4 | 7.9 | 11.4 | 1.8 | 57.0 |
| F | 4 | 0.1Pd/2.4Mn/ZrO2 | 2.1 | 75.4 | 69.9 | 1.1 | 6.0 | 7.1 | 14.2 | 1.7 | 52.7 |
|   | 5 | 0.1Pd—0.4Cu/2.4Mn/ZrO2 | | 77.7 | 71.1 | 1.5 | 6.4 | 7.2 | 12.2 | 1.7 | 55.2 |
| G | 4 | 0.1Pd/2.4Mn/ZrO2 | 2.2 | 70.6 | 70.9 | 0.7 | 5.4 | 7.4 | 13.7 | 1.9 | 50.1 |
|   | 5 | 0.1Pd—0.4Cu/2.4Mn/ZrO2 | | 72.9 | 72.6 | 0.9 | 5.7 | 7.4 | 11.8 | 1.8 | 52.9 |
| H | 4 | 0.1Pd/2.4Mn/ZrO2 | 2.4 | 62.2 | 71.9 | 0.3 | 4.7 | 7.9 | 13.0 | 2.2 | 44.7 |
|   | 5 | 0.1Pd—0.4Cu/2.4Mn/ZrO2 | | 63.6 | 74.5 | 0.4 | 4.7 | 7.8 | 11.1 | 1.9 | 47.4 |
| I | 6 | 0.02Ir/ZrO2 | 2.1 | 51.3 | 30.9 | 0.0 | 1.7 | 3.1 | 64.0 | 0.3 | 15.9 |
|   | 7 | 0.02Ir/2.6Mn/ZrO2 | | 69.7 | 66.5 | 1.4 | 4.8 | 6.3 | 19.3 | 1.7 | 46.4 |
|   | 8 | 0.02Ir/0.6Cu/ZrO2 | | 65.5 | 57.0 | 0.4 | 3.9 | 4.4 | 33.2 | 1.1 | 37.3 |
|   | 9 | 0.02Ir/0.6Cu/2.4Mn/ZrO2 | | 86.6 | 65.5 | 2.7 | 7.8 | 6.6 | 16.4 | 1.0 | 56.7 |
| J | 6 | 0.02Ir/ZrO2 | 2.2 | 48.6 | 31.7 | 0.0 | 1.6 | 3.3 | 63.0 | 0.4 | 15.4 |
|   | 7 | 0.02Ir/2.6Mn/ZrO2 | | 64.7 | 67.5 | 1.2 | 4.4 | 6.7 | 18.6 | 1.6 | 43.7 |
|   | 8 | 0.02Ir/0.6Cu/ZrO2 | | 61.7 | 57.3 | 0.3 | 3.6 | 4.5 | 33.2 | 1.1 | 35.4 |
|   | 9 | 0.02Ir/0.6Cu/2.4Mn/ZrO2 | | 84.1 | 66.4 | 2.3 | 7.4 | 6.9 | 14.5 | 2.5 | 55.8 |
| K | 6 | 0.02Ir/ZrO2 | 2.4 | 43.4 | 32.9 | 0.0 | 1.5 | 3.7 | 61.6 | 0.3 | 14.3 |
|   | 7 | 0.02Ir/2.6Mn/ZrO2 | | 55.6 | 69.0 | 0.9 | 3.8 | 7.7 | 16.7 | 1.9 | 38.4 |
|   | 8 | 0.02Ir/0.6Cu/ZrO2 | | 55.0 | 58.2 | 0.2 | 3.2 | 5.0 | 32.4 | 1.0 | 32.0 |
|   | 9 | 0.02Ir/0.6Cu/2.4Mn/ZrO2 | | 77.4 | 69.3 | 1.5 | 6.3 | 7.7 | 11.7 | 3.5 | 53.6 |
| L | 6 | 0.02Ir/ZrO2 | 2.6 | 38.9 | 33.6 | 0.0 | 1.4 | 4.1 | 60.6 | 0.3 | 13.1 |
|   | 7 | 0.02Ir/2.6Mn/ZrO2 | | 45.6 | 68.7 | 0.6 | 4.2 | 8.6 | 14.5 | 3.4 | 31.3 |
|   | 8 | 0.02Ir/0.6Cu/ZrO2 | | 49.7 | 59.5 | 0.1 | 2.9 | 5.8 | 30.7 | 1.0 | 29.6 |
|   | 9 | 0.02Ir/0.6Cu/2.4Mn/ZrO2 | | 71.9 | 72.5 | 1.1 | 5.8 | 8.7 | 9.6 | 2.3 | 52.1 |

Examples 10–14

Catalyst EXAMPLES 10–14 were prepared and tested using different procedures than for catalyst EXAMPLES 1–9, therefore their method of preparation and testing procedure are described below. The base metal was again manganese in these catalysts, and when it was used, it was added first to the zirconia or alumina support. Manganese nitrate [$Mn(NO_3)_2$], copper nitrate [$Cu(NO_3)_2$], and palladium nitrate [$Pd(NO_3)_2$] used to prepare the catalyst samples for EXAMPLES 10–14 were all purchased from Aldrich (Milwaukee, Wis.).

For EXAMPLE 10, a zirconia support was purchased from Süd-Chemie (Louisville, Ky.) in the form of particles (ca. 0.84–1.19 mm size or 16–20 mesh size). The zirconia support was thermally pretreated at 1,000° C. for about 6 hours at a ramp rate of 1.5° C./min.

Catalyst Preparation for EXAMPLES 10–14

Example 10

$0.1Pd-0.4Cu/2.4Mn/ZrO_2$

The pretreated zirconia support was impregnated with a solution of $Mn(NO_3)_2$ by incipient wetness technique. The amount of manganese salt was dissolved in enough water to infuse into the support particles without wetting the surface of the support, and to yield 2.4 wt % Mn in the final catalyst weight. The support spheres were then allowed for about 2 hours to given ample time to absorb the solution completely (conditioning) through the support from surface to center giving uniform distribution throughout. The wet sample was then dried in a oven at 80° C. for at least 2 hours. The dried sample was then calcined at atmospheric pressure and a temperature of about 125° C. for 1 hour to slowly evaporate any remaining water and then, using a heating ramp of 5° C./min from 125° C. to 500° C., the sample was calcined at a temperature of about 500° C. for 3 hours. Next, amounts of $Pd(NO_3)_2$ and $Cu(NO_3)_2$ were dissolved in a solution which was impregnated onto the manganese-modified calcined support sample. The amounts of $Pd(NO_3)_2$ and $Cu(NO_3)_2$ in the solution were sufficient to yield 0.1 wt % Pd and 0.4 wt % Cu in the final catalyst weight. The same conditions for impregnation, conditioning, drying, and calcining as described above were used for this step. The final composition of the catalyst was 0.1 wt % Pd, 0.4 wt % Cu, 2.4 wt % Mn with the remainder being zirconia.

Example 11

$0.1Pd/Al_2O_3$

The pretreated alpha-alumina support was impregnated with a solution of $Pd(NO_3)_2$. The amount of palladium salt was dissolved in enough water to infuse into the support particles without wetting the surface of the support, and to yield 0.1 wt % Pd in the final catalyst weight. The same conditions for impregnation, conditioning, drying, and calcining as described in EXAMPLE 10 were used.

Example 12

$0.1Pd$-$0.4Cu/Al_2O_3$

The pretreated alpha-alumina support was impregnated with a solution of $Pd(NO_3)_2$ and $Cu(NO_3)_2$ by incipient wetness technique. Amounts of copper and palladium salts were dissolved to yield 0.4 wt % Cu and 0.1 wt % Pd the final catalyst weight. The same conditions for impregnation, conditioning, drying, and calcining as described in EXAMPLE 10 were used. The final composition of the catalyst was 0.1 wt % Pd, 0.4 wt % Cu with the remainder being alumina.

Example 13

$0.1Pd$-$2.4Mn/Al_2O_3$

The pretreated alpha-alumina support was impregnated with a solution of $Mn(NO_3)_2$ by incipient wetness technique to yield 2.4 wt % Mn in the final catalyst weight. The same conditions for impregnation, conditioning, drying, and calcining as described in EXAMPLE 10 were used. Next, $Pd(NO_3)_2$ was dissolved in a solution which was impregnated onto the manganese-modified calcined sample. The same conditions for impregnation, conditioning, drying, and calcining as described earlier were used for this step. The final composition of the catalyst was 0.1 wt % Pd, 2.4 wt % Mn with the remainder being alumina.

Example 14

$0.1Pd$-$0.4Cu/2.4Mn/Al_2O_3$

The same procedure used for EXAMPLE 13 was used, except that a solution of $Pd(NO_3)_2$ and $Cu(NO_3)_2$ was applying to the manganese-modified support instead on a solution of $Pd(NO_3)_2$. The same conditions for impregnation, conditioning, drying, and calcining as described earlier were used. The final composition of the catalyst was 0.1 wt % Pd, 0.4 wt % Cu, 2.4 wt % Mn with the remainder being alumina.

Catalyst Performance Testing Procedure for EXAMPLES 10–14 at About 4 psig

Before testing, all catalyst samples of EXAMPLES 10–14 were first reduced in a furnace with an atmosphere with an equimolar mixture of nitrogen and hydrogen for 1 hour at 125° C., then brought to 500° C., and maintained at that temperature for 3 hours.

The reactor was a ½" inside diameter quartz tubing. The catalyst sample was packed to form a catalyst bed between two blank ceramic foams, one as catalyst bed support and another as shield. All tests for catalyst EXAMPLES 10–14 were done with 3 grams of inert alumina on top of the catalyst bed. The reactor feeds were supplied via gas cylinders. Ethane, molecular oxygen, and nitrogen came from gas cylinders. The flow rates of ethane, molecular oxygen, and nitrogen were controlled by gas flow controllers at 1661 standard cubic centimeters per minute (sccm), 639 sccm, and 750 sccm, respectively. An electric heater was located at the upstream of the catalyst bed and used to pre-heat the reactor feed to desired temperatures. The feed gases were mixed in a static mixer outside the reactor and heated before entering the catalyst bed; then the mixture was fed to the reactor. The inlet temperature, directly above the shield, was set at 300° C. A cooler was located downstream of the catalyst bed and used to rapidly cool product stream down to below 35° C. to condensate most of water vapor. A small part of the product gas stream was sent to a gas chromatograph for composition analyses. The tests were conducted with about 3 grams of each of the catalysts EXAMPLES 10–15 described above. The reactant gas mixture comprised $O_2$ and ethane, and the ethane-to-$O_2$ molar ratio of the feed was 2.6, with a total reactant gas mixture flow rate of 3 standard liters per minute (SLPM), corresponding to a gas hourly space velocity of about 75,000 hr$^{-1}$. All experiments were conducted at approximately atmospheric pressure (slightly above at 4 psig). The results are reported in Table 2, where $C_2H_4$, $C_2H_2$, and $CH_4$, represent ethylene, acetylene, and methane, respectively.

TABLE 2

Catalytic performance of EXAMPLES 10–14 at about 4 psig

| | | Catalysts | $C_2H_6$ to $O_2$ molar ratio | $C_2H_6$ conv., % | Selectivity, % | | | $C_2H_4$ Yield, % |
|---|---|---|---|---|---|---|---|---|
| | # | Composition | | | $C_2H_4$ | $C_2H_2$ | $CH_4$ | |
| M | 10 | $0.1Pd$—$0.4Cu/2.4Mn/ZrO_2$ | 2.6 | 53.0 | 71.7 | 0.4 | 11.5 | 38.0 |
| N | 11 | $0.1Pd/Al_2O_3$ | 2.6 | 38.1 | 58.6 | 0 | 6.4 | 22.3 |
| | 12 | $0.1Pd$—$0.4Cu/Al_2O_3$ | | 58.1 | 75.6 | 0.6 | 9.2 | 43.9 |

TABLE 2-continued

Catalytic performance of EXAMPLES 10–14 at about 4 psig

| # | Catalysts Composition | $C_2H_6$ to $O_2$ molar ratio | $C_2H_6$ conv., % | Selectivity, % | | | $C_2H_4$ Yield, % |
|---|---|---|---|---|---|---|---|
| | | | | $C_2H_4$ | $C_2H_2$ | $CH_4$ | |
| 13 | 0.1Pd—2.4Mn/$Al_2O_3$ | | 54.1 | 70.6 | 0.6 | 11.3 | 38.2 |
| 14 | 0.1Pd—0.4Cu/2.4Mn/$Al_2O_3$ | | 55.9 | 71.6 | 0.6 | 10.2 | 39.6 |

Catalyst Performance Testing Procedure for EXAMPLES 10 and 14 at About 45 psig

These two catalyst EXAMPLES 10 and 14 were tested at a higher reactor pressure of about 45 psig and using greater GHSV. The reactant gas mixture comprised $O_2$ and ethane, was preheated to about 300° C. and has an ethane-to-$O_2$ molar ratio of about 1.8. The two catalyst testing runs were conducted at a pressure of about 45 psig. The results are reported in Table 3, where $C_2H_4$, $C_2H_2$, and $CH_4$, represent ethylene, acetylene, and methane, respectively.

TABLE 3

Catalytic performance of EXAMPLE 10 and EXAMPLE 14 at 45 psig

| | # | Catalysts Composition | GHSV, hr$^{-1}$ | $C_2H_6$ to $O_2$ molar ratio | $C_2H_6$ conv., % | Selectivity, % | | | $C_2H_4$ Yield, % |
|---|---|---|---|---|---|---|---|---|---|
| | | | | | | $C_2H_4$ | $C_2H_2$ | $CH_4$ | |
| O | 10 | 0.1Pd—0.4Cu/2.4Mn/$ZrO_2$ | 500,000 | 1.8 | 92.8 | 56.4 | 4.4 | 12.0 | 52.3 |
| P | 14 | 0.1Pd—0.4Cu/2.4Mn/$Al_2O_3$ | 660,000 | 1.8 | 85.2 | 58.6 | 1.9 | 8.6 | 49.9 |

Examples 15 to 18

Catalyst Preparation for EXAMPLES 15–18

The same zirconia support material used in EXAMPLES 1–9 was used to prepare EXAMPLES 15–18. The base metal was manganese in these catalysts, and it was added first to the zirconia support. Soluble metal salts of manganese, copper and/or the promoter metal (rhodium or ruthenium) were employed for incipient wetness. Similarly to EXAMPLE 9, manganese nitrate [Mn(NO$_3$)$_2$] and copper nitrate [Cu(NO$_3$)$_2$] were used as respective precursors of manganese and copper. EXAMPLES 15–16 comprised rhodium as the promoter, and the rhodium precursor used to make the catalyst samples was rhodium(III) nitrate (Strem Chemicals, Newburyport, Mass.). EXAMPLES 17–18 comprised ruthenium as the promoter, and the ruthenium precursor used to make the catalyst samples was ruthenium(III) nitrosyl nitrate (Aldrich, Milwaukee, Wis.).

Example 15

0.01Rh/2.6Mn/100 ZrO2

This catalyst was first prepared as described in EXAMPLE 1, except that the amount of manganese loading was slightly higher at 2.6 wt %. Then the manganese-modified zirconia support was impregnated with a solution of a solution of rhodium(III) nitrate by incipient wetness technique. The same conditions for impregnation, conditioning, drying, and calcining as described in EXAMPLE 1 were used. The final composition of the catalyst was 0.01 g Rh and 2.6 g Mn per 100 g of zirconia support.

Example 16

0.01Rh/0.4Cu/2.4Mn/100 ZrO2

This catalyst was first prepared as described in EXAMPLE 1. Then the manganese-modified zirconia support was impregnated with a solution of Cu(NO$_3$)$_2$ and rhodium(III) nitrate. The same conditions for impregnation, conditioning, drying, and calcining as described in EXAMPLE 1 were used. The final composition of the catalyst was 0.01 g Rh, 0.4 g Cu, and 2.4 g Mn per 100 g of zirconia support.

Example 17

0.01Ru/2.6Mn/100 ZrO2

This catalyst was first prepared as described in EXAMPLE 1, except that the amount of manganese loading was slightly higher at 2.6 wt %. Then the manganese-modified zirconia support was impregnated with a solution of ruthenium(III) nitrosyl nitrate by incipient wetness technique. The same conditions for impregnation, conditioning, drying, and calcining as described in EXAMPLE 1 were used. The final composition of the catalyst was 0.01 g Ru and 2.6 g Mn per 100 g of zirconia support.

Example 18

0.01Ru/0.4Cu/2.4Mn/100 ZrO2

This catalyst was first prepared as described in EXAMPLE 1. Then the manganese-modified zirconia support was impregnated with a solution combining Cu(NO$_3$)$_2$ and ruthenium(III) nitrosyl nitrate. The same conditions for impregnation, conditioning, drying, and calcining as described in EXAMPLE 1 were used. The final composition of the catalyst was 0.01 g Ru, 0.4 g Cu, and 2.4 g Mn per 100 g of zirconia support.

Catalyst Performance Testing Procedure for EXAMPLES 15–18

Before testing similarly to EXAMPLES 1–9, all catalyst EXAMPLES 15–18 were reduced in an atmosphere with an equimolar mixture of hydrogen and nitrogen at 125° C. for 0.5 hour, then at 500° C. for 3 hours.

The catalyst EXAMPLES 15–18 were tested at a gas hourly space velocity of 354,000 hr$^{-1}$ using the same procedure as described for EXAMPLES 1–9. The results are reported in Table 4, where $C_2H_4$, $C_2H_2$, and $CH_4$, represent ethylene, acetylene, and methane, respectively. FIG. 1 illustrates the effect of copper on the ethylene yield of an ODH reaction using rhodium-promoted catalysts and ruthenium-promoted ODH catalysts based on a manganese-modified zirconia support.

V and W of Table 4, the addition of Cu (EXAMPLE 18) to a Ru promoted Mn catalyst on zirconia (EXAMPLE 17) resulted in an improved ethylene yield and a significantly better ethane conversion at an ethane-to-$O_2$ molar ratio of 2.0 and 2.6. Improvements in ethylene yield at higher fuel to $O_2$ ratios are particularly marked when an iridium, rhodium, or ruthenium promoter is modified with copper, as discussed in detail below and as can be seen in FIG. 1. The ethylene yield was almost identical for any of these 3 promoters for a given ethane-to-$O_2$ molar ratio from 2 to 2.6.

Palladium Promoted Manganese-based Catalyst

The experiments further show that, when palladium is used as the promoter, the primary benefit of copper modification is the resultant increase in yield of ethylene (see FIG. 1 for the improved ethylene yield for zirconia-based catalyst EXAMPLE 5 with copper compared to EXAMPLE 4 without copper; and for alumina-based catalyst EXAMPLE 14 with copper compared to EXAMPLE 13

TABLE 4

Catalytic performance of EXAMPLE 15–18 on zirconia at 4 psig

| | # | Catalysts Composition | $C_2H_6$ to $O_2$ molar ratio | $C_2H_6$ conv., % | Selectivity, % $C_2H_4$ | $C_2H_2$ | $CH_4$ | $C_2H_4$ Yield, % |
|---|---|---|---|---|---|---|---|---|
| Q | 15 | 0.01Rh/2.6Mn/ZrO$_2$ | 1.8 | 82.6 | 65.4 | 2.8 | 7.6 | 54.0 |
| R | 15 | 0.01Rh/2.6Mn/ZrO$_2$ | 2.0 | 67.2 | 62.8 | 0.9 | 3.8 | 42.2 |
|   | 16 | 0.01Rh—0.4Cu/2.4Mn/ZrO$_2$ |  | 88.0 | 63.2 | 3.2 | 8.7 | 55.6 |
| S | 15 | 0.01Rh/2.6Mn/ZrO$_2$ | 2.1 | 57.5 | 55.8 | 0.3 | 4.8 | 32.1 |
|   | 16 | 0.01Rh—0.4Cu/2.4Mn/ZrO$_2$ |  | 87.7 | 64.0 | 2.8 | 8.5 | 56.2 |
| U | 16 | 0.01Rh—0.4Cu/2.4Mn/ZrO$_2$ | 2.6 | 69.3 | 71.8 | 1.1 | 6.1 | 49.8 |
| V | 17 | 0.01Ru/2.6Mn/ZrO$_2$ | 2.0 | 56.6 | 65.7 | 0.6 | 5.5 | 37.2 |
|   | 18 | 0.01Ru—0.4Cu/2.4Mn/ZrO$_2$ |  | 80.6 | 68.2 | 6.7 | 1.9 | 55.0 |
| W | 17 | 0.01Ru/2.6Mn/ZrO$_2$ | 2.6 | 31.9 | 52.3 | 0.3 | 3.7 | 20.6 |
|   | 18 | 0.01Ru—0.4Cu/2.4Mn/ZrO$_2$ |  | 70.0 | 73.5 | 5.7 | 1.1 | 51.5 |

The effect of copper modification on alkane conversion, alkene selectivity and alkene yield are shown for a variety of catalyst compositions employing Pd, Ir, Rh and Ru on zirconia supports in Tables 1 and 4 above, and for a few catalyst compositions employing Pd and Ir on alumina supports in Tables 2 and 3 above. The effect of copper modification on ethylene yield for catalyst employing manganese-modified zirconia supports is also illustrated in FIG. 1. Copper addition to a base metal catalyst with a precious metal promoter shows surprising and unexpected positive results for the four promoters (Pd, Ir, Rh and Ru) used in these experiments. It can be seen that, in lines E, F, G, and H of Table 1 covering the effect of copper on catalytic performance of ODH catalysts in different ethane-to-$O_2$ molar ratios between 2.0 to 2.4, the addition of Cu (EXAMPLE 5) to a Pd promoted Mn catalyst on zirconia (EXAMPLE 4) resulted in higher ethylene selectivity and yield. Also the addition of Cu (EXAMPLE 9) to a Ir promoted Mn catalyst on zirconia (EXAMPLE 7) had a similar effect on the ethylene selectivity and yield (see line L in Table 1). In line N of Table 2, the addition of Cu (EXAMPLE 14) to a Pd promoted Mn catalyst on alumina (EXAMPLE 13) resulted in the same improved ethylene yield and selectivity at an ethane-to-$O_2$ molar ratio of 2.6. In lines R and S of Table 4, the addition of Cu (EXAMPLE 16) to a Rh promoted Mn catalyst on zirconia (EXAMPLE 15) showed an improved ethylene yield and ethane conversion at an ethane-to-$O_2$ molar ratio of 2.0 and 2.1. Similarly, in lines without copper). Referring now to the data in rows E-H in Table 1, ethane conversion is improved especially at low fuel to oxygen ratios (row E and F in Table 1), and as the fuel to oxygen ratio is increased from 2.0 to 2.4, both the ethane conversion and selectivity to ethylene are improved in the presence of copper (EXAMPLE 5) compared to a catalyst without copper (EXAMPLE 4). At about atmospheric pressure, the palladium-promoted Cu-modified Mn catalyst seemed to have a better ethane conversion and ethylene yield when supported on alumina (EXAMPLE 14; Line N on Table 2) than when supported on zirconia (EXAMPLE 10; Line M on Table 2); whereas the ethylene selectivity seemed similar with both supports. On the other end, at a higher pressure of about 45 psig, the palladium-promoted Cu-modified Mn catalyst had a better ethane conversion and ethylene yield when supported on zirconia (EXAMPLE 10; Line O on Table 3) than when supported on alumina (EXAMPLE 14; Line P on Table 3); whereas the ethylene selectivity was better with the catalyst supported on alumina (EXAMPLE 14).

Iridium Promoted Manganese-based Catalysts

The present experiments demonstrated, as is illustrated in FIG. 1, the surprising increase in the yield of ethylene with a copper-modified, iridium-promoted manganese catalyst (EXAMPLE 9) compared to an iridium-promoted manganese catalyst without copper (EXAMPLE 7). The data in rows I-L in Table 1 show that, while the iridium on zirconia catalyst is relatively poor as an olefins catalyst, the combination of iridium and manganese (EXAMPLE 7) or the combination of iridium and copper (EXAMPLE 8) improved both the ethane conversion and the selectivity to ethylene. Still further, the copper-modified, iridium-promoted manganese catalyst (EXAMPLE 9) gave marked improvement for both ethane conversion and ethylene selectivity (and therefore ethylene yield) as compared to the iridium and copper, or the iridium and manganese catalysts (EXAMPLES 8 and 9, respectively). The drastic improvement observed by combining the three metals (Ir, Cu, and Mn) is unexpected. And the large improvement is observed over a wide range of fuel to oxygen ratios and is greater at higher ratios, which is also unexpected.

Rhodium Promoted Manganese-based Catalysts

The present experiments demonstrated, as is illustrated in FIG. 1, the surprising increase in the yield of ethylene with a copper-modified, rhodium-promoted manganese catalyst (EXAMPLE 16) compared to a rhodium-promoted manganese catalyst without copper (EXAMPLE 15). The data in rows R-S in Table 4 showed that a rhodium promoter on a manganese catalyst was relatively poor as an olefins catalyst as the ethylene yield rapidly decreased from about 54% to about 32% as the ethane-to-$O_2$ molar ratio increased from 1.8 to 2.1, the addition of copper in rhodium-promoted manganese catalyst (EXAMPLE 16) gave marked improvement for ethane conversion and therefore ethylene yield at the higher ethane-to-$O_2$ molar ratios in which it was expected that rhodium-promoted catalyst without copper would have performed poorly. Therefore the drastic improvement observed in ethylene yield by combining the three metals (Rh, Cu, and Mn) was quite unexpected. And the large improvement was observed over a wide range of ethane to oxygen ratios and resulted in olefin yield similar to that observed with the Ir-promoted copper-modified manganese catalyst (EXAMPLE 9) at higher ratios, which was also unexpected.

Ruthenium Promoted Manganese-based Catalysts

Finally, the present experiments demonstrated, as is illustrated in FIG. 1, the surprising increase in the yield of ethylene with a copper-modified, ruthenium-promoted manganese catalyst (EXAMPLE 18) compared to a ruthenium-promoted manganese catalyst without copper (EXAMPLE 17). The data in rows V-W in Table 4 showed that a ruthenium promoter on a manganese catalyst (EXAMPLE 17) could generate ethylene at ethane-to-$O_2$ molar ratios of 2.2 and 2.6 albeit at a much lower yield than the copper-modified ruthenium-promoted manganese catalyst (EXAMPLE 18). The addition of copper to a ruthenium-promoted gave marked improvement for ethane conversion and therefore ethylene yield at the higher ethane-to-$O_2$ molar ratios, such that the ethylene yields obtained with ruthenium -were quite similar to those obtained with iridium-promoted or rhodium-promoted catalysts (EXAMPLES 9 and 16 respectively). Therefore the drastic improvement observed in ethylene yield by combining the three metals (Ru, Cu, and Mn) was also quite unexpected.

Hence it can be seen that the use of copper as a modifier for various promoted metal ODH catalysts can significantly improve ethylene yields. The improvement is demonstrated for iridium-, palladium-, rhodium- and ruthenium-promoted catalysts, and it is believed that similar results can be achieved when other promoters, such as platinum, nickel, iron, cobalt or osmium, are used. Likewise, it is believed that this improvement will not be limited to catalyst systems in which manganese is the base metal.

The following commonly assigned copending applications are hereby incorporated herein by reference: Attorney Docket No. 1856-18900, application Serial No. 10/266,404, filed Oct. 8, 2002 and entitled "Oxidative Dehydrogenation of Hydrocarbons Using Catalysts With Trace Promoter Metal Loading", published at Publication No. 2004/0068148, and Attorney Docket No. 1856-30100, Ser. No. 10/266,405, filed Oct. 8, 2002 and entitled "Rare Earth Metals as Oxidative Dehydrogenation Catalysts.", published at Publication No. 2004/0068153. In addition, the commonly-owned U.S. patent application with publication number 2003/0040655 filed Mar. 26, 2002 and entitled "Oxidative dehydrogenation of ailcanes to olefins using an oxide surface"is also hereby incorporated herein by reference. The disclosures of all other patents, patent applications and publications cited herein are hereby incorporated herein by reference, to the extent that they provide exemplary, procedural or other details supplementary to those set forth herein. Should the disclosure of any of the patents, patent applications, and publications that are incorporated herein conflict with the present specification, however to the extent that such disclosure might render a term unclear, the present specification shall take precedence.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention.

Accordingly, the scope of protection is not limited by the description set out above, but is limited only by the claims that follow, that scope including all equivalents of the subject matter of the claims. Each and every claim is incorporated into the specification as an embodiment of the present invention. Thus the claims are a further description and are an addition to the preferred embodiments of the present invention. Use of the term "optionally" with respect to any element of a claim is intended to mean that the subject element may or may not be present. Both alternatives are intended to be within the scope of the claim.

Finally, the discussion of a reference in the Background is not an admission that it is prior art to the present invention, especially any reference that may have a publication date after the priority date of this application.

What is claimed is:

1. An oxidative dehydrogenation catalyst comprising
    a non-copper base metal selected from the group consisting of metals of Groups 2, 4–7 and 11–13 metals of the Periodic Table of Elements, scandium, yttrium, actinium, iron, cobalt, nickel, their oxides and combinations thereof;
    copper;
    optionally, a promoter comprising a metal from Groups 8, 9, and 10 of the Periodic Table of Elements, and
    a support comprising aluminum oxide, zirconium oxide, silicon nitride, magnesium oxide, or mixtures thereof;
    wherein copper is present at between about 0.0001 and 10 weight percent of the total catalyst weight, and the catalyst has a molar ratio of copper to the base metal of about 1:10 or higher.

2. The catalyst of claim 1 wherein the molar ratio of copper to the base metal is between about 1:10 and about 1:2.

3. The catalyst of claim 1 wherein copper is present at between about 0.01 and 2 weight percent of the total catalyst weight.

4. The catalyst of claim 1 wherein the base metal comprises an element selected from the group consisting of manganese, chromium, gold, their corresponding oxides, and combinations thereof.

5. The catalyst of claim 1 wherein the base metal comprises manganese.

6. The catalyst of claim 1 wherein the promoter comprises an element selected from the group consisting of platinum, palladium, iridium, rhodium, ruthenium, or any combinations thereof.

7. The catalyst of claim 1 wherein the catalyst comprises a promoter metal, and the promoter metal is palladium, rhodium, ruthenium, or iridium.

8. The catalyst of claim 1 wherein the support is pretreated using a technique selected from the group consisting of heating, spray-drying, dehydrating, drying, steaming and calcining.

9. The catalyst of claim 8 wherein the pretreatment comprises heating the support at a temperature between about 1,000° C. and 1,500° C. for 0.5 to 10 hours at a heating ramp rate between 0.5 and 3° C./min.

10. An oxidative dehydrogenation catalyst comprising
between 0.05 wt % and 20 wt % manganese;
between 0.001 wt % and 10 wt % copper;
optionally, between 0.005 wt % and 0.2 wt % of a promoter metal selected from the group consisting of palladium, iridium, rhodium, ruthenium, platinum, and any combination thereof; and
a support comprising zirconia, alumina, or combinations thereof.

11. The oxidative dehydrogenation catalyst of claim 10 wherein the catalyst comprises between 0.1 wt % and 2 wt % copper.

12. The oxidative dehydrogenation catalyst of claim 10 wherein the catalyst comprises between 2 wt % and 6 wt % manganese.

13. The oxidative dehydrogenation catalyst of claim 10 wherein the catalyst has a molar ratio of copper to manganese greater than about 1:10.

14. The oxidative dehydrogenation catalyst of claim 10 wherein the catalyst comprises a promoter metal, and the molar ratio of the base metal to the promoter metal is at least about 10.

15. The catalyst of claim 10 wherein the support is pretreated using a technique selected from the group consisting of heating, spray-drying, dehydrating, drying, steaming and calcining.

16. The catalyst of claim 15 wherein the pretreatment comprises heating the support at a temperature between about 1,000° C. and 1,500° C. for 0.5 to 10 hours at a heating ramp rate between 0.5 and 3° C./min.

17. An oxidative dehydrogenation catalyst comprising
manganese;
copper;
a promoter metal selected from the group consisting of palladium, iridium, platinum, rhodium, ruthenium, and combinations thereof; and
a refractory support,
wherein the catalyst has a molar ratio of copper to manganese greater than about 1:20.

18. The oxidative dehydrogenation catalyst of claim 17 wherein the catalyst comprises between 0.1 wt % and 2 wt % copper.

19. The oxidative dehydrogenation catalyst of claim 17 wherein the catalyst comprises between 2 wt % and 6 wt % manganese.

20. The oxidative dehydrogenation catalyst of claim 17 wherein the catalyst has a molar ratio of copper to manganese of about 1:10 or higher.

21. The oxidative dehydrogenation catalyst of claim 17 wherein the molar ratio of the manganese to the promoter metal is at least about 10.

22. The oxidative dehydrogenation catalyst of claim 17 wherein the refractory support includes a material selected from the group consisting of zirconia, stabilized zirconia, alumina, stabilized alumina, silicon nitride, magnesium oxide, and combinations thereof.

23. The oxidative dehydrogenation catalyst of claim 22 wherein the material is selected from the group consisting of zirconia, stabilized zirconia, alumina, stabilized alumina, and combinations thereof.

24. A method for making an oxidative dehydrogenation catalyst comprising
impregnating a base metal-containing precursor onto a support;
calcining said base metal-modified support;
impregnating a solution comprising copper and optionally a Groups 8, 9, or 10 promoter metal, onto said base metal-modified support to form a copper-modified catalyst precursor;
calcining said copper-modified catalyst precursor; and
reducing said calcined catalyst precursor to obtain a copper-modified catalyst.

25. The method of claim 24 wherein the copper-modified catalyst comprises between 0.001 wt % and 10 wt % copper.

26. The method of claim 24 wherein the copper-modified catalyst comprises between 0.005 wt % and 0.2 wt % of the Groups 8, 9, or 10 promoter metal.

27. The method of claim 24 wherein the promoter metal is palladium, iridium, platinum, rhodium, ruthenium, or any combination thereof.

28. The method of claim 24 wherein the support comprises zirconia, stabilized zirconia, alumina, stabilized alumina, silicon nitride, magnesium oxide, or any combination thereof.

29. The method of claim 24 wherein the copper-modified catalyst has a molar ratio of copper to base metal greater than about 1:20.

30. The method of claim 24, further comprising the step of pretreating the support using a technique selected from the group consisting of heating, spray-drying, dehydrating, drying, steaming and calcining prior to the impregnation of the base metal-containing precursor onto the support.

* * * * *